(12) United States Patent
Accisano, III et al.

(10) Patent No.: US 7,578,814 B2
(45) Date of Patent: Aug. 25, 2009

(54) DRAINAGE CATHETER WITH LOCKABLE HUB

(75) Inventors: Nicholas Gerald Accisano, III, Howell, NJ (US); Fred P. Lampropoulos, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 686 days.

(21) Appl. No.: 11/198,642

(22) Filed: Aug. 5, 2005

(65) Prior Publication Data

US 2007/0032779 A1    Feb. 8, 2007

(51) Int. Cl.
*A61M 27/00*    (2006.01)
*A61M 1/00*    (2006.01)

(52) U.S. Cl. .................. 604/541; 604/540; 604/543; 604/544; 604/533; 600/585

(58) Field of Classification Search ................. 600/585; 604/541, 540, 542, 543, 544, 533
See application file for complete search history.

(56) References Cited

U.S. PATENT DOCUMENTS

| | | | |
|---|---|---|---|
| 5,399,165 A | 3/1995 | Paul, Jr. ........................ 604/95 |
| 5,693,083 A * | 12/1997 | Baker et al. ................. 623/1.11 |
| 6,508,789 B1 * | 1/2003 | Sinnott et al. .......... 604/164.02 |
| 6,673,060 B1 | 1/2004 | Fleming, III ................ 604/540 |
| 6,699,233 B2 * | 3/2004 | Slanda et al. ............... 604/533 |
| 7,087,038 B2 * | 8/2006 | Lee .......................... 604/95.04 |
| 7,217,256 B2 * | 5/2007 | Di Palma .................... 604/104 |
| 2004/0059293 A1 * | 3/2004 | Chu et al. .................... 604/107 |
| 2005/0070821 A1 * | 3/2005 | Deal et al. .................. 600/585 |
| 2005/0107739 A1 * | 5/2005 | Palma ........................ 604/104 |

* cited by examiner

*Primary Examiner*—Tatyana Zalukaeva
*Assistant Examiner*—Susan Su
(74) *Attorney, Agent, or Firm*—Ryan D. Benson; Stoel Rives LLP (57) ABSTRACT

A reversible lockable drainage catheter for use in draining excess bodily fluid in a tissue having a catheter tube with a proximal end and a distal end, and a lockable hub positioned about the catheter tube. A suture of the drainage catheter can be reversibly tensioned, and locked in the tensioned conformation by depressing one or more surfaces of the lockable hub. The suture can then be released also by depressing one or more surface of the lockable hub, or by implementing one or more additional safety release mechanisms. For example, a safety release can be pulled in a proximal direction to release a tensioned suture. Similarly, the suture can be tensioned to a point that stretches an attachment point of the drainage catheter tube, and also causes the suture and safety release mechanism to disengage.

14 Claims, 6 Drawing Sheets

DRAINAGE CATHETER WITH LOCKABLE HUB

BACKGROUND OF THE INVENTION

1. The Field of the Invention

This present invention relates to systems and apparatus for draining bodily fluid from a patient.

2. Background and Relevant Art

Drainage catheters are used in a variety of medical settings for draining fluids from a patient's body. For example, a patient may suffer an injury, or have a medical problem where a bodily tissue stores an excess amounts of fluid, such as blood, or other bodily serum. If the fluid is not removed further complications in the patient can occur such as rupturing or infection of the tissue. Accordingly, drainage catheters have been developed to remove these fluids from the patient, to either relieve pressure, or to otherwise ensure the fluid build up does not result in tissue injury.

Conventional drainage catheters typically comprise a handle, an elongate catheter tube communicatively connected to the handle, and a flexible tip that includes a plurality of drainage bores. The drainage bores of the flexible tip allow communication of fluid through the elongate catheter tube. The practitioner inserts the tip and catheter tube into the patient's body, such that the tip enters the tissue or area of fluid build up. The user then pulls a suture, which extends from the handle, passes along the length of the catheter tube, and is secured to the tip. When the practitioner pulls or retracts the suture, the tip flexes inward toward the catheter tube, thereby forming a curved loop having drainage bores within the fluid build up area.

To hold the suture in place in order to maintain the curved configuration of the catheter tube, the practitioner either must hold the suture and catheter with two hands, or secure the suture to the catheter handle by wrapping the suture around the handle. Unfortunately, securing the catheter handle in this manner can be somewhat insecure and inconvenient, especially if the catheter is to remain in place for an extended period of time. In the event that additional manipulation or repositioning of the catheter tube must be utilized, it can be difficult to unwrap the suture from the handle for proper manipulation of the length of catheter.

Once the tip of the catheter tube is appropriately positioned, the excess fluid then flows into the individual drainage bores of the tip, flows along the length of the catheter tube, and is drained from the catheter hub. Thereafter, the practitioner will remove the catheter from the localized area. Unfortunately, the curved conformation of the tip relative to the catheter tube makes it difficult to remove the drainage catheter from its drainage position. In particular, removing the drainage catheter while the tip is still in an inwardly flexed position can cause the drainage catheter to tear or otherwise damage bodily tissue. Accordingly, the practitioner typically attempts to straighten the tip before removing the catheter. Generally, this requires at a minimum releasing the suture that caused the tip to flex in the first instance. Where the suture has been wrapped to maintain the curved configuration of the tip of the drainage catheter, unwrapping of the suture can be difficult and time consuming.

Furthermore, when the practitioner releases the suture, the flexible tip on the conventional catheter will not fully release in a manner that allows manipulation of the catheter tip into a substantially straight position. This can be due to a variety of factors. For example, if the drainage catheter is in the patient's body for an extended period of time, the bodily fluids or articles and materials associated with the bodily fluids may encrust the suture thread preventing release of the curved configuration of the tip of the drainage catheter. This can cause the suture to remain in a tensile configuration even after the practitioner has, for example, unwrapped the suture about the handle. Thus, a practitioner may need to perform additional procedures, such as invasive surgery, to remove the catheter.

Accordingly, an advantage in the art can be realized with systems and apparatus that conveniently provide fluid drainage within a patient's body, and that can be removed with minimal complication.

BRIEF SUMMARY OF THE INVENTION

The present invention relates to a system and apparatus for draining fluid from a patient's body in a safe and convenient manner, and for removing the catheter tubes and apparatus safely upon completion. In particular, embodiments of the present invention relate to a drainage catheter having a locking mechanism for securing a suture once the suture has been tensioned. Additional embodiments provide for one or more release mechanisms, which reliably release the suture, and reliably allow the tip to relax into a substantially straight position.

For example, in one embodiment of the present invention, a drainage catheter comprises a hub having a depressible button to secure or release the suture. A suture extends from within the hub, through a catheter tube, out through a tip. The suture exits the tip, and terminates at an attachment point on the distal portion of the catheter tube. When the practitioner pulls the suture, the suture pulls against the stylet, causing the tip to flex toward the catheter tube in a looping fashion. The practitioner can then depress the depressible button, causing the suture to be clamped inside the hub thus maintaining the looped configuration of the tip. Bodily fluid then enters the tip, travels through the catheter tube, and exits through a proximal portion of the catheter tube.

Upon completion, the catheter hub allows the suture to release in a reliable fashion, hence, allowing the tip to straighten in order to withdraw the catheter tube from the patient. For example, the practitioner can release the depressible button, such that the suture is no longer clamped. In another embodiment, the practitioner can draw the stylet proximally toward the hub, causing the distal end of the suture to be released from the stylet at the catheter tube attachment point. In still another embodiment, the attachment point of the catheter tube can be configured such that the attachment point stretches with added tension or pressure, and provides sufficient room for the suture to slip off the stylet. In each case, a relaxed suture allows for straightening of the tip.

Additional features and advantages of exemplary embodiments of the invention will be set forth in the description which follows, and in part will be obvious from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention relates to drainage catheter relates to a system and apparatus for draining fluid from a patient's body in a safe and convenient manner, and for removing the catheter tubes and apparatus safely upon completion. In particular, embodiments of the present invention relate to a drainage catheter having a locking mechanism for securing a suture once the suture has been tensioned. Additional embodiments provide for one or more release mechanisms, which reliably release the suture, and reliably allow the tip to relax into a substantially straight position.

For example, as will be understood from the following drawings, a drainage catheter in accordance with the present invention can be described in one of primarily two conformations: a relaxed conformation, and a tensioned conformation. In the relaxed conformation (e.g., FIG. 1A), the drainage catheter can be straightened from its naturally curved configuration, and thus can be conformed primarily along one axis from a proximal end to a distal end of the catheter. In general, the relaxed conformation is preferable for inserting and removing the drainage catheter inside and away from the patient's body. A stylet, guide wire, or other straightening mechanism can be used to ensure the straightened configuration of the distal end of the catheter during insertion of the catheter tube.

By contrast, the tensioned conformation (e.g., FIG. 1B) is generally preferable for draining bodily fluid. For example, in the tensioned conformation, the distal end of the catheter tube is secured adjacent a more proximal portion of the catheter tube of the drainage catheter, due to a tensioning of the suture. In the tensioned conformation, the drainage bores at the catheter distal end typically face inwardly, or away from a patient's tissue. As such, the tensioned conformation is preferable for maintaining the drainage catheter inside the patient's body and removing excess fluid.

To facilitate efficient transition between the tensioned and relaxed conformations, a drainage catheter in accordance with the present invention comprises a lockable hub. For example, as will be understood more fully from the present description and claims, when one hub component is depressed or "locked", a suture is substantially prevented from proximal or distal motion, and can therefore allow the drainage catheter to hold a tensioned configuration without difficulty. Similarly, when releasing the hub component, or when actuating another hub component, the hub is "unlocked". This allows the suture to move in either a proximal or distal direction as necessary, which allows tensioning or relaxation of the catheter tip as desired.

Although these hub components used to accomplish efficient locking and releasing can be several and varied in shape, form, and/or specific function, the following description is directed to a number of specific features for one exemplary configuration. For example, the illustrated lockable hub includes a reversibly depressible button that, when depressed, engages one or more other components in a manner that the components, alone or in combination secure the suture from proximal or distal movement. When the button is pressed in a reverse direction, the suture is released, and the suture can therefore move in either a proximal or distal direction. Embodiments of the present invention also include a quick release mechanism, which provides redundant mechanisms for facilitate releasing of the flexible tip of the drainage catheter in the event that one release mechanism does not release the suture due to mechanical failure or encumbrance of the catheter with biological materials. Accordingly, embodiments of the present invention provide a drainage catheter that can be efficiently, safely, and reliably secured in a tensioned configuration while providing reliable releasing for repositioning or removal of the catheter tube from the patient.

Figure 1A:
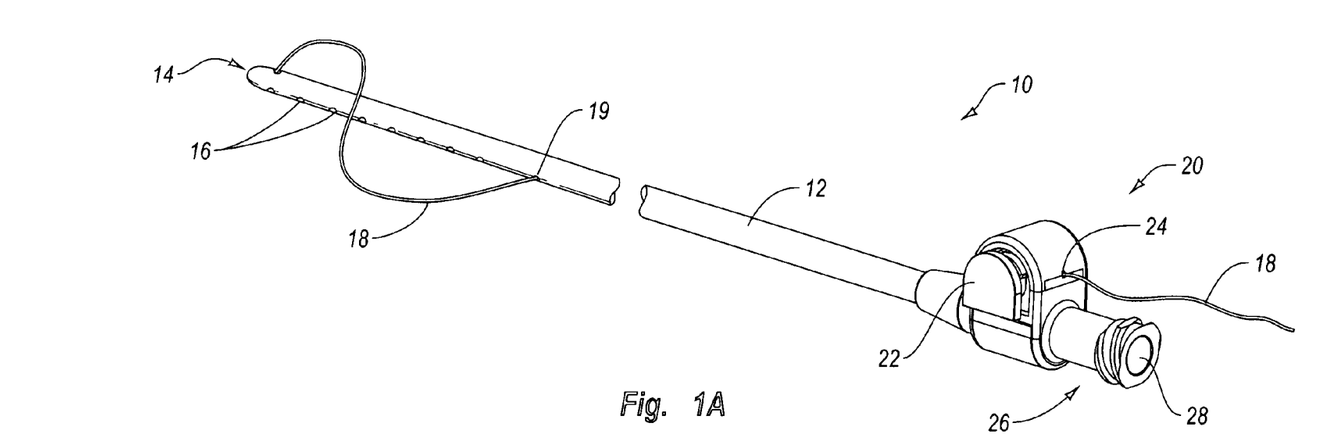
FIG. 1A illustrates a drainage catheter in which a suture is in a relaxed position, and a lockable hub is unlocked in accordance with one embodiment of the present invention.

FIG. 1A illustrates a drainage catheter 10 which comprises: (i) a catheter tube 12 having a proximal end 26 and a resiliently flexible distal end 14 including drainage bores 16. The resiliently flexible distal end 14 is in fluid communication with the catheter tube 12. The drainage catheter 10 also comprises (ii) a lockable hub 20 positioned at a point between the proximal end 26 and the distal end 14; and (iv) a suture 18, which extends from a cavity 24 of the hub 20, along the length of the catheter tube 12, exits the distal end 14, and loops rearward terminating at an attachment point 19. As will be understood from the present description and claims, the lockable hub 20 further comprises a number of internal components configured for efficiently securing and releasing suture 18. In addition, the distal end 14 of the catheter tube 12 can comprise any type of materials that provide flexible resilience, such as natural or synthetic rubber, flexible plastic, and so forth.

FIG. 1A also shows that the suture 18 is in a relaxed state, so that the distal end 14 is substantially straight relative to the proximal end 26. By way of explanation, the suture 18 can comprise any materials that can be pulled, released, tensioned, or relaxed, such as natural or synthetic fibers wound into a string, memory metals such as Nitinol wire, and so forth. In general, when the suture 18 is in a relaxed state, the drainage catheter 10 is in an appropriate conformation (i.e., straightened, or relaxed conformation) to be inserted into a patient, or to be withdrawn from the patient. In other words, the straightened or relaxed conformations of the catheter tube 12 and distal end 14 are more efficient for inserting and removing the drainage catheter 10 to or from a patient. In one embodiment, the suture 18 is threaded through the drainage catheter 10 via a sidewall bore (not shown), which is a separate lumen which runs along at least a portion of the length of catheter tube 12.

The drainage catheter 10 depicted in FIG. 1A is shown in an unlocked configuration, such that a depressible button 22, which extends from the lockable hub 20, extends outwardly. In the illustrated unlocked conformation, the suture 18 is free to move in either a proximal or a distal direction relative to the catheter tube 12 and hub 20. As will be understood more fully from these and the following Figures, however, the practitioner can depress the button 22 with respect to the hub 20, to secure the suture 18 inside the hub 20, so that the suture 18 is held at a certain degree of tension. To insert the drainage catheter 10 into a patient, a practitioner inserts the distal end 14 of the drainage catheter 10 in the relaxed conformation into an appropriate bodily tissue or cavity where excess fluid may exist.

Figure 1B:
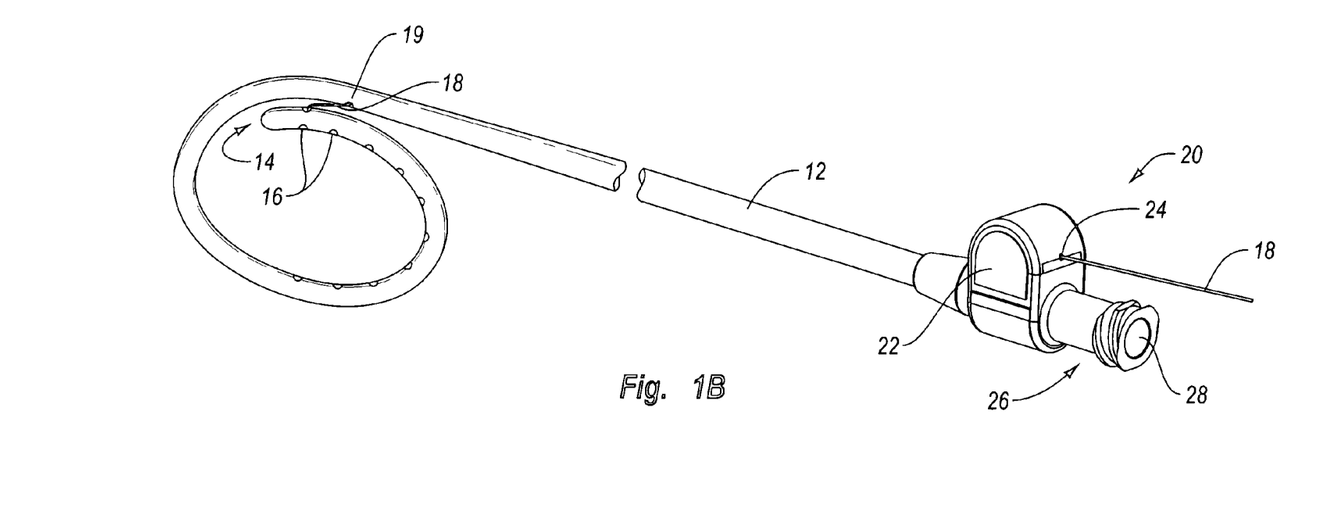
FIG. 1B illustrates the drainage catheter of FIG. 1A, wherein the suture is in a tensioned configuration, and the lockable hub has been locked to secure the tensioned configuration of the suture.

With reference now to FIG. 1B, once in the appropriate position, the practitioner then tensions the suture 18, such as by pulling the suture 18 in a proximal direction. This causes the distal end 14 of the drainage catheter 10 to flex inwardly toward the catheter tube 12 and form a loop, such that the drainage bores 16 are exposed on an inside of the formed loop. As previously described, the drainage bores 16 face on the inside of the formed loop in this tensioned conformation so as to avoid contact between the drainage bores 16 and bodily tissue (not shown). This minimizes blockage of the drainage bores 16 by the bodily tissue. In the tensioned conformation shown in FIG. 1B, bodily fluid enters drainage bores 16 of the catheter tube 12 at the distal end 14, and follows the fluid communication pathway of the distal end 14 and catheter tube 12. The bodily fluid ultimately exits through a cavity 28 at the proximal end 26 of the drainage catheter 10.

To hold the tensioned conformation of the suture 18, and hence the tensioned conformation of the distal end 14 relative to the catheter tube 12, FIG. 1B shows that button 22 has also been engaged, thereby locking the hub 20. As will be further described in the following figures, when the button 22 is depressed toward the drainage catheter 10, one or more components inside the lockable hub 20 engage suture 18 in combination with one or more other components, such that suture 18 cannot be moved through the groove 24. In particular, the engaged, or locked, conformation shown in FIG. 1B substantially prohibits the suture 18 from moving in either a proximal or a distal direction along the catheter tube 12 and distal end 14.

Figure 1C:
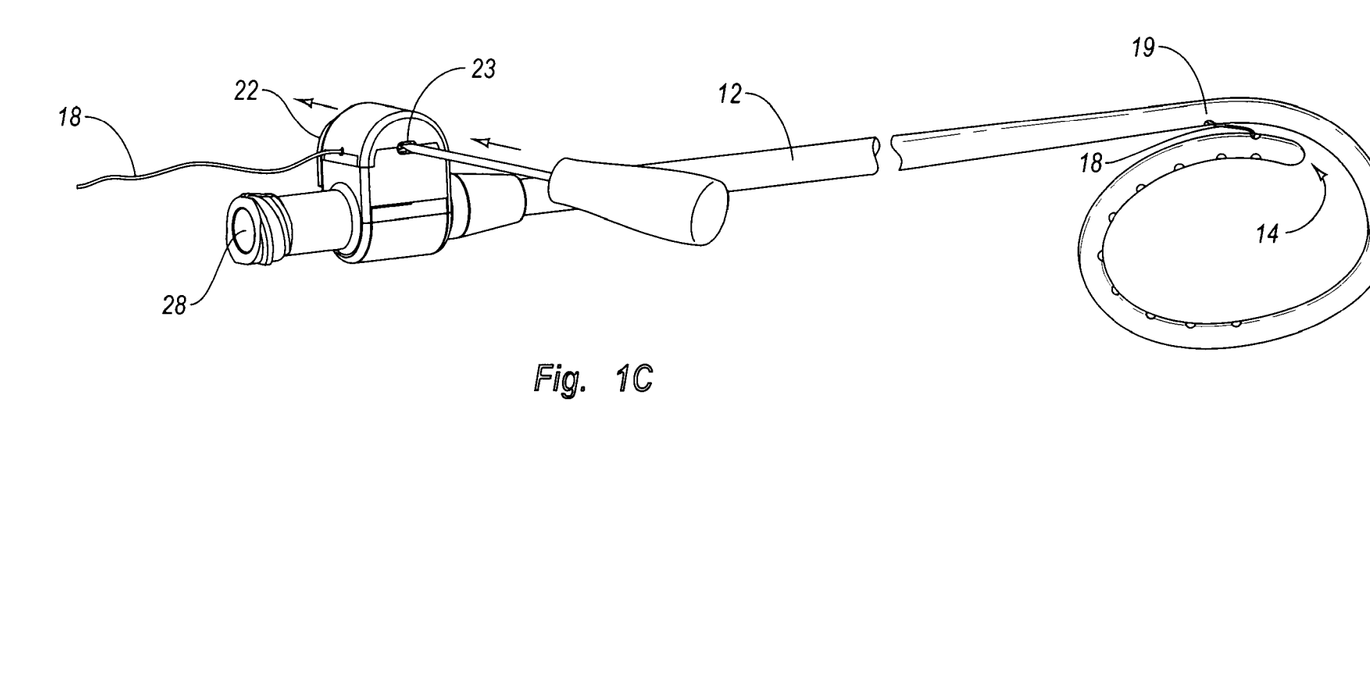
FIG. 1C illustrates the drainage catheter of FIG. 1B, further illustrating a mechanism for unlocking the lockable hub.

FIG. 1C is a perspective view of drainage catheter illustrating unlocking of hub 20 subsequent to completion of drainage of bodily fluid. For example, as shown in FIG. 1C, a practitioner can depress an opposing side 23 of the button 22, such as with a screw driver, a hemostat, or other appropriate pointed implement. By positioning the opposing side 23 of button 22 in a depression, inadvertent releasing of the suture is avoided. Once the hub 20 becomes unlocked, the suture 18 is released by the internal components of the lockable hub, which was used to secure the suture in the first instance. As such, the suture 18 will typically and naturally relax without additional tensioning, which thereby releases the tensioning of the flexible distal end 14 of drainage catheter 10, and can allow the distal end 14 to relax into a substantially straight conformation (or to be positioned into a substantially straight conformation). For example, the practitioner can pull the drainage catheter 10 in a proximal direction, and the distal end 14 will straighten to fit through the point of insertion. In another embodiment, to accommodate for an event in which the suture remains stuck, or tensioned, embodiments of the present invention further include a safety release which will be described in greater detail with reference to FIG. 2A.

Figures 2A, 2B:
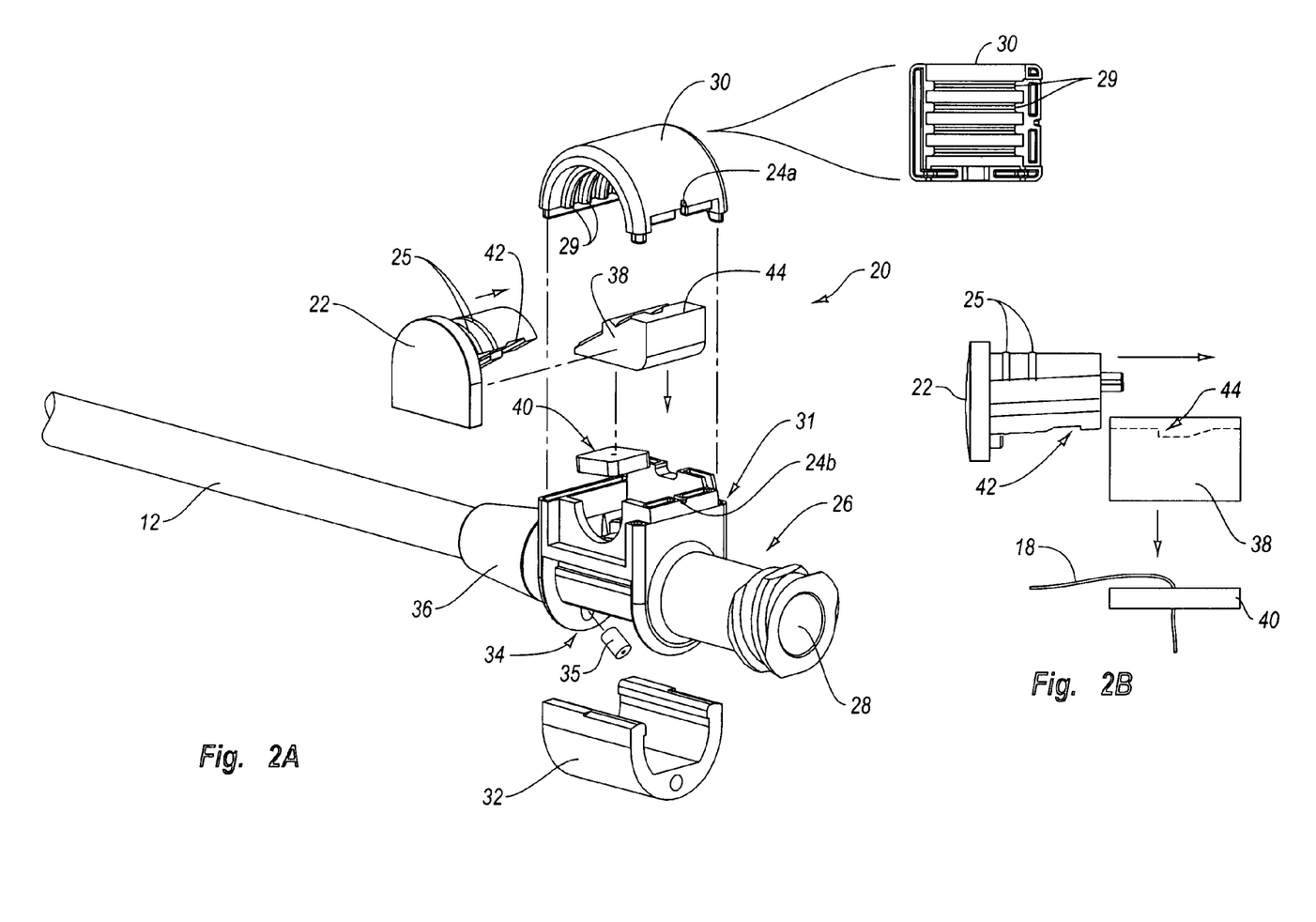
FIG. 2A illustrates an exploded view of a drainage catheter hub in accordance with one embodiment of the present invention.
FIG. 2B illustrates a close up side view of a depressible button and clamp member that is positioned inside the lockable hub.

FIG. 2A illustrates an exploded view of the hub 20 and a number of components in accordance with an embodiment of the present invention that can be used to pinch or otherwise hold the suture 18 in one or more positions. As shown, the drainage catheter hub 20 comprises: (i) an upper cap 30 having an upper groove 24a formed therein; (ii) a depressible button 22 configured be depressed inwardly; (iv) a clamp member 38, configured to move in cooperation with the depressible button 22; (v) a suture seal 40 configured to minimize leakage of bodily fluids from the catheter tube into the drainage catheter hub 20; (vi) a body 31, having a lower groove 24b formed therein; (vii) a sheath 36 that connects the hub 20 with the catheter tube 12; (viii) a lower cap 32; (ix) a release wire 34; and (x) a securement member 35 for attaching release wire 34 to lower cap 32. The hub 20 and related components can comprise any materials such as plastics or rubber, and/or metals, as necessary.

FIG. 2A also shows that the depressible button 22 can be configured to be held in place with respect to the upper cap 30. In particular, the major surface of button 22 comprises one or more ribs 25 that interlock with one or more alternating ribs 29 on the minor surface of the upper cap 30. In both cases, the ribs 25 of the button 22 and the ribs 29 of the upper cap 30 can be as flexible or rigid (or alternating flexible and/or rigid) as desired, and can be formed from any number of suitable materials. The depressible button 22 further comprises an inclined minor surface configured to complement an inclined major surface of the clamp member 38. The action of the depressible button 22 with respect to the clamp member 38 is described in greater detail in the following FIGS. 2B through 2F.

FIG. 2A further illustrates one position of the release wire 34 with respect to the hub 20. Generally, the release wire 34 may be any elongate component capable of extending from the hub 20 through to attachment point 19 (e.g., FIGS. 1A-1C). For example, the release wire 34 can comprise any suitable memory material, such as Nitinol, metal or metal alloys, synthetic materials, and so forth. The release wire 34 is positioned inside a sidewall stylet (not shown) formed in a wall of the catheter tube 12, such that the release wire 34 is not in direct contact with fluids flowing through the main catheter tube 12 lumen 28.

In addition, the release wire 34 can be attached to lower cap 32 to form a safety release, which is essentially a main gripping point for pulling the release wire 34 in a proximal direction. To operate the safety release in one embodiment, the practitioner at least partially detaches, slides, unhinges, or removes the lower cap 32 from the hub main body 31, thereby exposing the release wire 34. In other embodiments, the hub 20 is configured so that the safety release extends from the lower cap 32, or from the hub 20 generally, without separation or removal of any portion of the hub 20. As will be understood from the following Figures, the safety release provides a releasable attachment interface for the suture 18 within attachment point 19 (e.g., FIG. 1A).

Referring again to the operation of the depressible button 22 and clamp member 38, FIG. 2B shows that when the depressible button 22 is pushed inward, or toward an opposing side of the lockable hub 20, the depressible button 22 forces the clamp member 38 to move downward. In particular, pushing the depressible button 22 inward (toward an opposing side of the lockable hub 20) engages the corresponding inclines or declines of the minor surface of the button 22 and the major surface of the clamp member 38. When these surfaces engage, the upper cap 30 prevents the button 22 from rising upward, and thus causes the clamp member 38 top be pushed downward. Furthermore, the ribs 29 of upper cap 30 hold the button 22 in one or more positions as it is depressed in the lockable hub. When the clamp member 38 is forced downward, clamp member 38 places pressure on suture seal 40, and thereby clamps the suture 18 in position.

FIG. 2B also shows that the depressible button 22 and clamp member 38 include corresponding grooves 42 and 44, which can be used in addition to ribs 25 and 29 to secure the depressible button 22. That is, FIG. 2B shows that depressible button 22 includes a groove 42 in its minor, slanted surface, while clamp member 38 includes a corresponding groove 44 in its major, also slanted, surface. Thus, when depressible button 22 is pushed inward toward the opposing side of the drainage catheter 10, the depressible button slides along the clamp member 38 until it reaches a point where an end portion of the depressible button fits snugly within the groove 44 of the clamp member 38. As such, at least these corresponding grooves 42 and 44 can substantially prevent the depressible button 22 from being accidentally released, or from sliding back in the reverse direction.

Figure 2C:
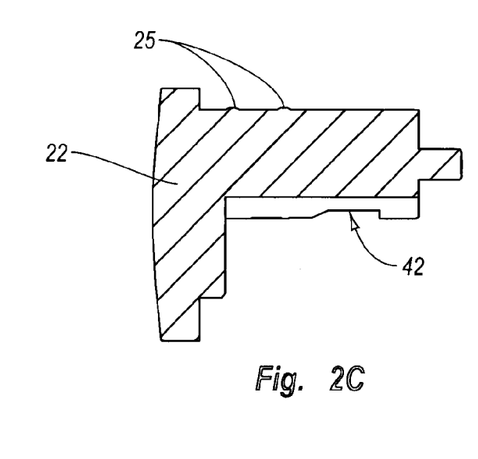
FIG. 2C illustrates a side cross-sectional view of the depressible button shown in FIGS. 2A and 2B.
Figure 2D:
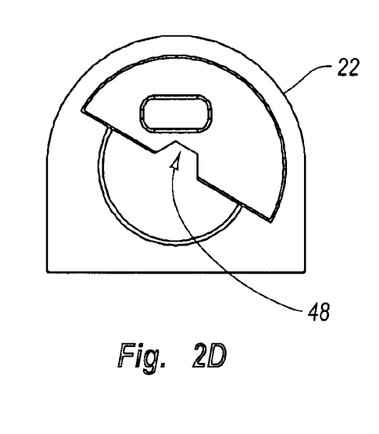
FIG. 2D illustrates an end view of the depressible button.

FIGS. 2C through 2F show that the depressible button 22 and clamp member 38 also include one or more additional protrusions and/or grooves, which are similarly configured for guiding and/or for securing the depressible button 22 and clamp member 38 together. For example, FIGS. 2C and 2D show alternating views of the depressible button 22, where FIG. 2C shows a side view, and FIG. 2D shows a front view that opposes the depressible side view shown in FIG. 2A. In particular, FIG. 2C shows that the depressible button includes the ribs 25, as well as the groove 42, which is configured to allow the depressible button 22 to interlock with the clamp member 38 in at least one position. FIG. 2D further illustrates that the depressible button 22 includes another groove 48 that is perpendicular to groove 42. In one embodiment, groove 48 is configured to guide the depressible button along a corresponding track or protrusion configured on or within the clamp member 38.

Figure 2E:
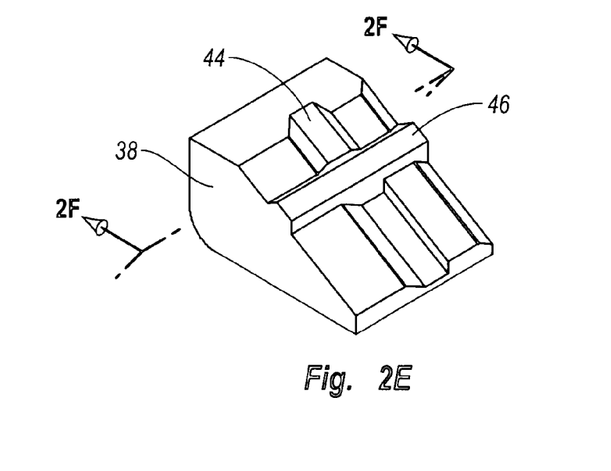
FIG. 2E illustrates a perspective view of the clamp member shown in FIGS. 2A and 2B.
Figure 2F:
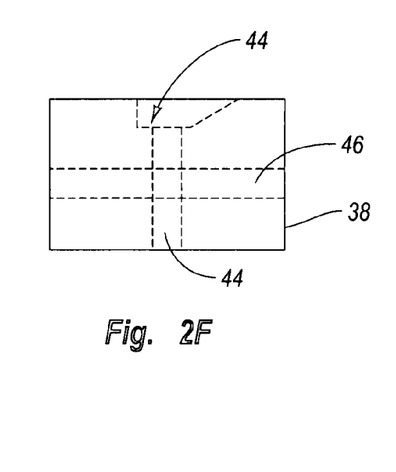
FIG. 2F illustrates a rear view of the clamp member shown in FIGS. 2A and 2B.

In particular, FIG. 2E shows that the clamp member 38 includes a track or protrusion 46 on its major surface, which is configured to slidably engage groove 48 of the depressible button 22. The track or protrusion 46 is perpendicular (see also FIG. 2F) to the groove 44, just as groove 48 is perpendicular to groove 42 of the depressible button 22. Thus, as the depressible button 22 is pushed along track or protrusion 46, the clamp member 38 guides the depressible button 22 until grooves 42 and 44 are aligned in a lockable or overlapping fashion.

The depressible button 22 and clamp member 38 can also be disengaged simply by providing sufficient pressure to a reverse side of the depressible button 22. This is possible in at least one embodiment since the depressible button 22 and/or clamp member 38 can be made at least partially of flexible materials. In one aspect, the materials are generally rigid enough to prohibit accidental disengagement, while being sufficiently flexible to allow purposeful disengagement. As such, sufficient pressure can cause the locked portion of the depressible button 22 and/or the non-grooved portion of the clamp member 38 to bend somewhat, and thus allow the depressible button 22 and clamp member 28 to move in opposite directions along track or protrusion 46. Accordingly, FIGS. 2A through 2F illustrate that the lockable hub 20 can include a wide range of alternatively configured components that are configured in a wide variety of formations for ensuring reliable, efficient, and reversible locking of the suture 18.

Figure 3A:
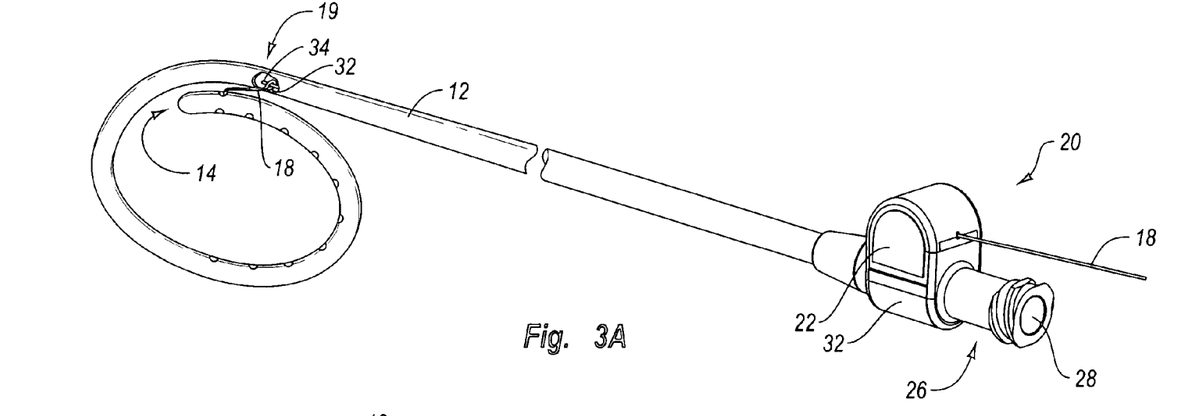
FIG. 3A is a perspective view of a drainage catheter, wherein the suture is secured to a stylet, in accordance with one embodiment of the present invention.
Figure 3B:
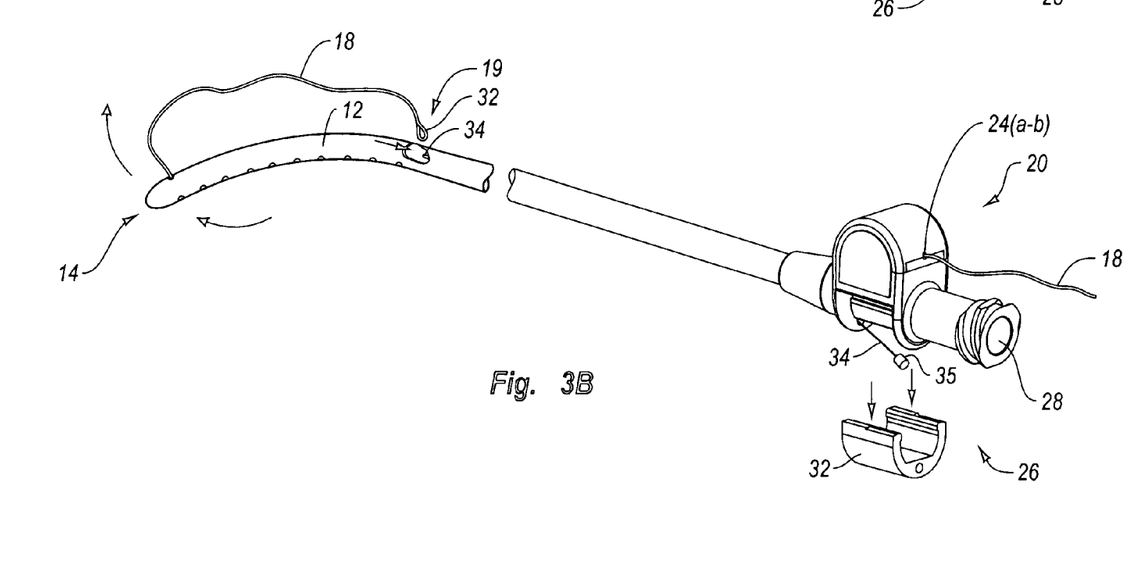
FIG. 3B is a perspective view of the drainage catheter in FIG. 3A, wherein the stylet is retracted releasing the suture.

FIGS. 3A and 3B illustrate alternate views of safety release 35 aspect of the lockable hub 20. In particular, FIGS. 3A and 3B show conformations where the suture 18 is secured to the release wire 34 at attachment point 19, and wherein the release wire 34 is subsequently detached from the suture 18 when the lower cap 32 is moved in a proximal direction. For example, as shown in the tensioned conformation of 3A, the release wire 34 has been inserted through a loop or knot at the end of the suture 18. This allows the suture 18 to be tensioned since, when the suture is pulled in a proximal direction, the suture 18 pulls against the release wire 34, which further causes a relative shortening of the release wire inside the catheter tube 12 relative to the length of the catheter tube 12. This shortening of the suture 18 therefore causes the flexible distal end 14 to bend inward toward the catheter tube 12. FIG. 3A further shows that the practitioner has locked this conformation by depressing the button 22 inward toward the opposing side of the lockable hub 20. As previously described, this locking of the hub 20 holds the suture 18 in a tensioned conformation, such that the distal end 14 is held in the tensioned, or curved conformation as required during the course of the procedure.

As shown in FIG. 3B, the practitioner may release the distal end 14 to a relaxed conformation by drawing the release wire 34 in a proximal direction. In this embodiment, the practitioner lowers or removes the lower cap 32 thus retracting the release wire 34. As the practitioner continues to retract or pulls the lower cap 32, the release wire 34 is moved in a proximal direction. This action causes the stylet 34 to detach from, for example, a loop in the suture 18 at attachment point 19. As a result, the suture 18 is free to move into a relaxed or "free" conformation. Furthermore, since the suture 18 is relaxed, there is no more additional tension being applied to the distal end 14 of the drainage catheter 10, and thus the flexible distal end 14 can also be straightened for readjustment or removal as desired.

Figure 4:
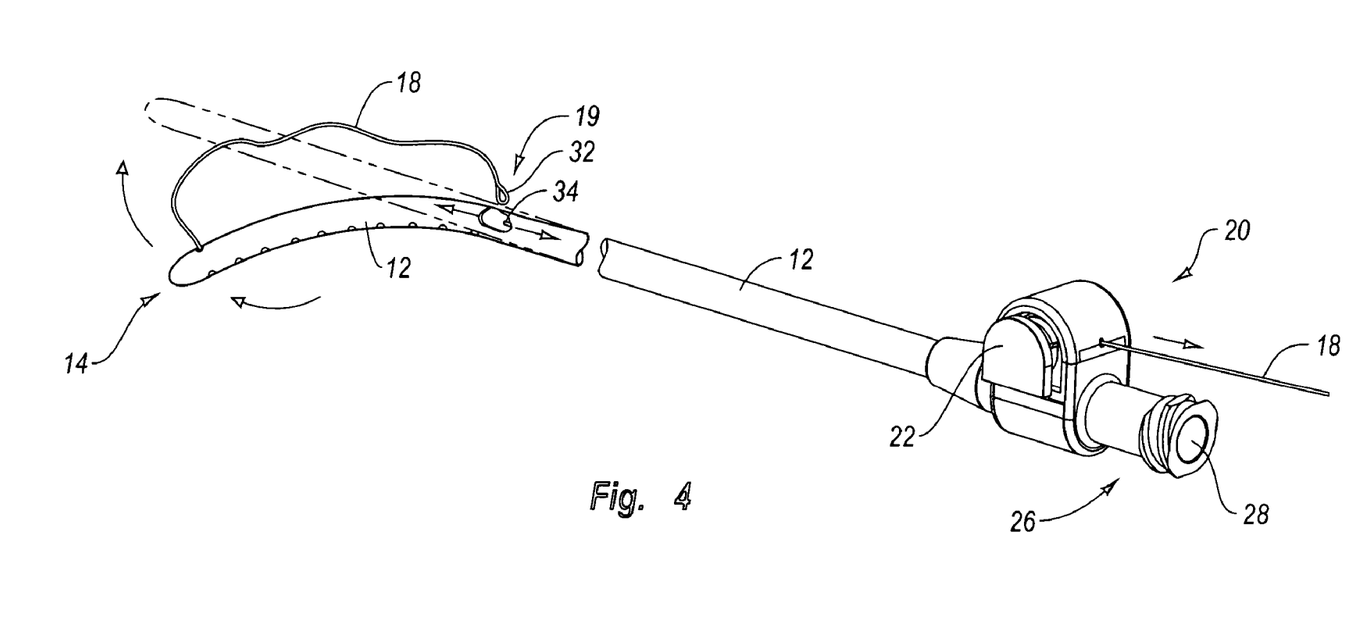
FIG. 4 illustrates a drainage catheter in which the catheter tube is configured such that when excessive force is exerted on the catheter tube, the suture is automatically released from the stylet and the tip of the catheter tube is straightened in accordance with an embodiment of the present invention.

FIG. 4 illustrates another embodiment of a drainage catheter 10, in which the catheter tube 12 comprises one or more memory materials, which are configured to allow the release wire 34 and suture 18 to detach without necessarily needing to pull safety release 35. In particular, FIG. 4 shows that attachment point 19 is positioned such that when an excessive amount of force is exerted on catheter tube 12, suture 18 is automatically released. The automatic releasing of suture 18 occurs before the amount of force exerted on the catheter tube results in injury to the patient. In other words, in the event that the practitioner attempts to retract catheter tube 12 from the patient without first releasing the looped configuration of the distal end 14 of catheter tube 12, the suture will automatically release the looped configuration of the distal end 14 of catheter tube before the tension on the catheter tube 12 is sufficient to cause injury to the patient.

For example the catheter tube 12, and/or distal end 14 (or simply the materials forming the portion of the catheter tube 12 at the attachment interface 19) can comprise flexible or resilient materials, such as natural or synthetic rubber, flexible plastics, memory metals, and the like. As the tension on catheter tube 14 increases catheter tube 14 stretches such that attachment point 19 moves past the end of release wire 34 allowing suture 18 to slip off release wire without rearward movement of release wire 34. The positioning of the tip of release wire 34 relative to attachment point 19 and the resilient properties of catheter tube is configured to provide yet another means for ensuring safe, and reliable relaxation of the distal end 14. In another embodiment, the configuration of the attachment point is such that when excessive force is exerted on the catheter tube, the attachment point stretches to release the suture.

Accordingly, a variety of embodiments of the embodiments are provided herein for safely, reliably, efficiently, and reversibly securing a drainage catheter in a tensioned or relaxed conformation. In particular, embodiments of the present invention provide a number of components that can be used to ensure that a suture is locked in one or more positions as desired by a practitioner. Additional embodiments of the present invention provide for other components, or aspects of the previously described locking components, that allow the suture to retain a relaxed conformation, and which therefore allow the drainage catheter also to move back to a substantially straight conformation. Still further embodiments provide a number of safety mechanisms for ensuring that the drainage catheter can retain a relaxed conformation even in the event of other complicating circumstances, such as clogging, or sticking of the suture.

One will appreciate that the embodiments described herein can also be combined with each other, and can also be substituted with one or more other, suitable components within the context of the invention. For example, another alternative embodiment of a drainage catheter 10 may comprise a lockable hub as described herein, and also include the safety release and release wire 34, as well as a stretchable attachment point 19. Alternatively, a drainage catheter in accordance with the present invention can include other components, such that depression of one or more components causes the suture to hold a certain position. For example, another embodiment of a lockable hub might include a resiliently deformable dome positioned on the side of the lockable hub. When the dome is pushed a first time, a locking mechanism moves to a first position which locks the suture. When the button is pushed a second time, the locking mechanism is moved to a second position, and thereby releases the suture.

Accordingly, there are a wide variety of means, components, and apparatus that would be suitable for accomplishing the functions described herein. In particular, the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. A drainage catheter for use in aspirating excess bodily fluids comprising:
    a catheter tube having a proximal end in fluid communication with a distal end, wherein fluid that enters one or more drainage bores at the distal end exit the catheter tube at the proximal end;
    a suture attached to the catheter tube at an attachment point, the suture extending from a distal position of the catheter tube to a proximal portion of the catheter tube;
    a lockable hub comprising:
        a body;
        a depressible button having at least a portion thereof positioned within the body, the depressible button having an inclined surface; and
        a clamp member operably disposed relative to the depressible button, the clamp member having an inclined surface which is slidable relative to the inclined surface of the depressible button wherein a user biases the depressible member in a direction transverse to the axis of extension of the catheter tube such that the button slides in a transverse direction relative to the body causing the inclined surface of the depressible button to slidably engage the inclined surface of the clamp member urging the clamp member in a downward direction to secure the position of the suture relative to the lockable hub.

2. The drainage catheter as recited in claim 1, wherein the lockable hub secures the suture in one position when the depressible button is pushed in one direction, and releases the suture when the depressible button is pushed in an opposite direction.

3. The drainage catheter as recited in claim 2, wherein the depressible button cooperatively engages a clamp member, such that depression of the depressible button causes the clamp member to substantially hold the suture in position.

4. The drainage catheter as recited in claim 3, wherein the depressible button comprises a sloped minor surface having one or more grooves, and wherein the clamp member comprises a sloped major surface having one or more corresponding grooves or tracks that align with the one or more grooves of the button.

5. The drainage catheter as recited in claim 4, wherein at least one of the grooves of the depressible button is configured to slidably engage a protrusion of the clamp member, and wherein an end portion of the depressible button is configured to reversibly lock with a groove of the clamp member.

6. The drainage catheter as recited in claim 1, wherein the catheter tube comprises a sidewall bore through which the suture is threaded, whereby the suture is separated from bodily fluid flowing through the catheter tube.

7. The drainage catheter as recited in claim 1, further comprising a release wire that extends from the hub to the attachment point of the catheter tube.

8. The drainage catheter as recited in claim 7, wherein the release wire comprises a memory material such as Nitinol.

9. The drainage catheter as recited in claim 7, wherein the catheter tube comprises a sidewall bore in communication with the attachment point of the catheter tube, wherein the release wire is threaded through the sidewall bore.

10. The drainage catheter as recited in claim 7, wherein the release wire includes a safety release that can be pulled in a proximal direction, such that pulling the safety release in the proximal direction detaches the release wire from the suture at the attachment point.

11. The drainage catheter as recited in claim 7, wherein the catheter tube is configured with a resilient cavity at the attachment point such that, upon a force exerted on the suture, the resilient cavity stretches to a larger size and allows the suture to detach from the release wire.

12. A suture release system in a drainage catheter comprising:
    a hollow catheter tube having a distal end for receiving fluid, and a proximal end for dispersing fluid received from the distal end;
    a suture that extends along the hollow catheter tube, and attaches at an attachment point at the distal end of the hollow catheter tube; and a lockable hub in communication with the hollow catheter tube, the lockable hub comprising:
- an upper cap having one or more ribs extending from a minor surface thereon;
- a depressible button having one or more ribs formed on a major surface thereon; and
- a clamp member configured for cooperative engagement with the depressible button, such that engagement with the depressible button in one direction causes the clamp member to hold the suture, and such that engagement with the depressible button in an opposite direction causes the clamp member to release the suture, wherein the clamp member is configured such that one or more grooves and one or more tracks on a major surface of the clamp member cooperatively enguage corresponding grooves on a minor surface of the depressible button, and
- a plate positioned opposite the major surface of the clamp member, such that cooperative engagement of the depressible button and clamp member causes the clamp member to press against the plate.

13. A suture locking system in a drainage catheter comprising:
- a hollow catheter tube having a distal end for receiving fluid, and a proximal end for dispersing fluid received from the distal end;
- a suture that extends along the hollow catheter tube, and attaches at an attachment point at the distal end of the hollow catheter tube; and
- a lockable hub in communication with the hollow catheter tube, the lockable hub comprising:
  - a depressible button having an angled portion perpendicular to a depressible surface;
  - a clamp member having a reciprocal angled portion that abuts the angled portion of the button on one side, and abuts the suture on an opposing side, wherein the clamp member is urged in a downward direction to press against the suture in a longitudinal direction when the depressible button is moved toward the clamp member in a lateral direction.

14. A suture locking system as recited in claim 13, wherein the lockable hub further comprises a release wire that extends from the lockable hub to the attachment point on the hollow catheter tube.

* * * * *

UNITED STATES PATENT AND TRADEMARK OFFICE
CERTIFICATE OF CORRECTION

PATENT NO.        : 7,578,814 B2                                        Page 1 of 1
APPLICATION NO.   : 11/198642
DATED             : August 25, 2009
INVENTOR(S)       : Accisano, III et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1040 days.

Signed and Sealed this

Seventh Day of September, 2010

David J. Kappos
*Director of the United States Patent and Trademark Office*